(12) United States Patent
Staton

(10) Patent No.: US 7,876,962 B2
(45) Date of Patent: Jan. 25, 2011

(54) MULTI-GAIN PHOTODETECTION SYSTEM FOR ARRAY ANALYSIS

(75) Inventor: Kenneth L. Staton, San Carlos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 523 days.

(21) Appl. No.: 10/912,427

(22) Filed: Aug. 4, 2004

(65) Prior Publication Data

US 2006/0031029 A1     Feb. 9, 2006

(51) Int. Cl.
*G06K 9/52*     (2006.01)
(52) U.S. Cl. ......................................... 382/194; 702/32
(58) Field of Classification Search ........................ None
See application file for complete search history.

(56) References Cited

U.S. PATENT DOCUMENTS

| | | | |
|---|---|---|---|
| 7,013,220 B2 * | 3/2006 | Dorsel et al. ................... | 702/19 |
| 7,062,092 B2 * | 6/2006 | Kaushikkar et al. ......... | 382/213 |
| 2003/0165871 A1 | 9/2003 | Corson et al. | |
| 2003/0168579 A1 | 9/2003 | Corson et al. | |
| 2003/0203371 A1 | 10/2003 | Corson et al. | |
| 2004/0021911 A1 | 2/2004 | Corson et al. | |
| 2004/0023224 A1 | 2/2004 | Corson et al. | |
| 2004/0064264 A1 | 4/2004 | Corson et al. | |

OTHER PUBLICATIONS

Cheung et al. "Making and Reading Microarrays" Nature America Inc- Nature Genetics Supplement (1999) 21:15-18.

* cited by examiner

*Primary Examiner*—Marjorie Moran
*Assistant Examiner*—Jason M Sims

(57) ABSTRACT

Methods for evaluating a pixel signal produced during scanning of a chemical array are provided. In general, the methods involve producing at least two analog signals for a pixel using a multi-gain signal detection system, integrating at least one of these signals, and outputting data representing the pixel. Also provided are systems and computer program products for performing the subject methods, and an array scanner containing these systems and program products.

21 Claims, 3 Drawing Sheets

MULTI-GAIN PHOTODETECTION SYSTEM FOR ARRAY ANALYSIS

BACKGROUND OF THE INVENTION

Arrays of surface-bound binding agents may be used to detect the presence of particular targets, e.g., biopolymers, in solution. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate, such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In certain instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many array based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

For each pixel of a scan, a light detector (e.g., a photomultiplier tube) typically detects light emitted from the surface of a microarray, and outputs an analog signal that changes in amplitude according to the amount of emitted light entering the detector. This analog signal is usually sampled and digitized using an analog-to-digital converter (A/D converter) and integrated using a digital signal processor (DSP) to provide data, e.g., a numerical evaluation of the brightness of the pixel. This data is usually stored and analyzed at a later date.

However, current data processing methodologies are limited in their capacity to obtain reliable data from every pixel of a scan because there is a limitation to the amplitude of input signals of system components in current signal detection systems. For example, the signal output of a detector may exceed the signal input range of a current-to-voltage converter, or the output of a current-to-voltage converter may exceed the signal input range for an analog-to-digital converter. Accordingly, for many bright areas of a scan, the analog signal produced by a light detection system may be partially or fully "saturated", i.e., at the maximum amplitude. Because of this limitation, an integrated signal representing a pixel may not always accurately represent the amount of light entering the detector. Despite this limitation, saturated signals are typically digitized and integrated using similar methods to those for non-saturated signals, leading to inaccurate data.

Accordingly, there is a great need for a signal integration system that can increase the accuracy of data obtained from a saturated pixels. The present invention meets this, and other, needs.

Literature of interest includes: published U.S. patent applications: 20030168579, 20030165871, 20040064264, 20040023224, 20040021911, 20030203371 and 20030168579; and Cheung et al., Nature Genetics 1999, 21: 15-19.

SUMMARY OF THE INVENTION

Methods for evaluating a pixel signal produced during scanning of a chemical array are provided. In general, the methods involve producing at least two analog signals for a pixel using a multi-gain signal detection system, integrating at least one of these signals, and outputting a single integrated signal representing the pixel. In certain embodiments, the methods involve detecting, integrating and outputting a signal for a non-saturated input signal for the pixel. Also provided are systems and computer program products for performing the subject methods, and an array scanner containing these systems and products. The subject invention finds use in a variety of different applications, including both genomics and proteomics applications.

In one embodiment, the invention provides a system for evaluating a pixel signal produced during scanning a chemical array. The system generally comprises: a) a multi-gain detection system that produces a plurality of analog signals representative of a pixel; b) a converter for digitizing the plurality of analog signals to produce a set of digital signals for each analog signal; and, c) a signal processor that: i) identifies a set of non-saturated digital signals for the pixel, and ii) integrates the set of non-saturated digital signals for said pixel, to evaluate the pixel.

In certain embodiments, the multi-gain detection system comprises one or more of a photodetector (e.g., a PMT or the like), a single multi-gain detector, a plurality of detectors each having a different gain setting, a plurality of current-to-voltage converters or a multi-gain voltage amplifier. In certain embodiments the converter comprises a plurality of analog-to-digital converters.

The invention also provides a chemical array scanner including a laser excitation system, and a subject system for evaluating a pixel signal, as described above. In certain embodiments, the chemical array scanner produces data for an array, and the scanner contains a storage medium (e.g., computer memory) for storing the data.

The invention also provides a method for evaluating a pixel during scanning of a chemical array. In general, this methods includes: producing a plurality of analog signals for said pixel using a multi-gain signal detection system; identifying a non-saturated analog signal for the pixel; and integrating the non-saturated analog signal for said signal, to evaluate the pixel. The plurality of signals may be a plurality of voltage or current signals.

In certain embodiments, the subject method for evaluating a pixel includes: providing for detection of a set of non-saturated digital signals for said pixel; integrating a set of digital signal that is non-saturated; and outputting a single integrated signal for said set of digital signals that are not saturated. In particular embodiments, the single integrated signal is data, and said method further comprises storing the data on a computer-readable medium.

The invention also provides a computer-readable medium that contains programming for execution by a digital signal processor to produce data for a pixel represented by multiple sets of digital signals of varying magnitude, the programming including: instructions for integrating a set of non-saturated digital signals for said pixel to produce an integrated signal representing said signal; and outputting said integrated signal to produce data for said pixel. In certain embodiments, the computer-readable medium further includes instructions for executing the programming when a non-saturated signal for said pixel is detected. In particular embodiments, programming provides for tagging the output of the processor to indicate that the data is from a saturated pixel.

The invention also provides a processor comprising the above-described computer-readable medium, and a chemical array scanner including or in communication with such a processor.

In other embodiments, the invention provides a method of assaying a sample. This method generally includes: (a) contacting the sample with a chemical array of two or more chemical ligands immobilized on a surface of a solid support; and (b) reading the array with the above-described chemical array scanner to obtain data. In particular embodiments, the reading step of this method may include: producing a plurality of analog signals for a pixel using a multi-gain signal detection system to produce sets of digital signals for the pixel; identifying a set of non-saturated analog signals for the pixel; and integrating the non-saturated analog signal for said signal, to produce data for said pixel.

The invention provides a method including transmitting a result obtained from any of the above-described methods from a first location to a remote location, and a method including receiving data representing data obtained by any of the above-described methods.

The invention also provides a kit for use in a chemical array optical scanner, containing: (a) a computer-readable medium according to the above; and (b) at least one chemical array.

In any of the above embodiments, the array may be a nucleic acid or polypeptide array.

DEFINITIONS

Figure 1:
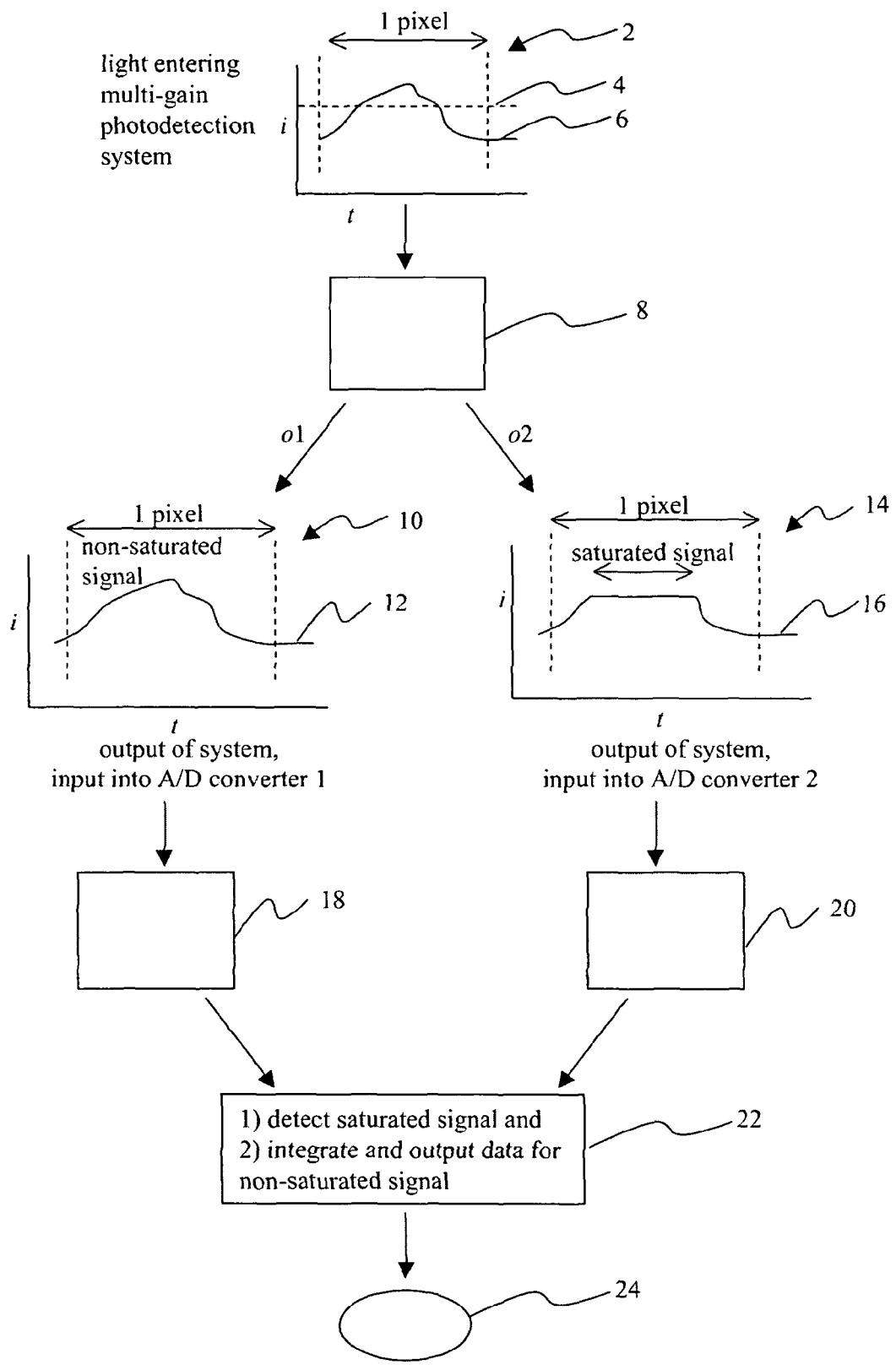
FIG. 1 schematically illustrates many general features of the multi-gain detection systems described herein.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), polypeptides (which term is used to include peptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," or "chemical array" includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. Nos. 5,599,695, 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). If a device is "in communication with" another device, the devices are capable of transmitting or data or instructions to each other. Such devices may be networked to each other. "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "scanner" is device for evaluating arrays. In scanners, an optical light source, particularly a laser light source, generates a collimated beam. The collimated beam is focused on the array and sequentially illuminates small surface regions of known location (i.e. a position) on an array substrate. The resulting signals from the surface regions are collected either confocally (employing the same lens used to focus the light onto the array) or off-axis (using a separate lens positioned to one side of the lens used to focus the light onto the array). The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". Arrays are often scanned and/or scan results are often represented at 5 or 10 micron pixel resolution. To achieve the precision required for such activity, components such as the lasers must be set and maintained with particular alignment. Scanners may be bi-directional, or unidirectional, as is known in the art.

The scanner typically used for the evaluation of arrays includes a scanning fluorometer. A number of different types of such devices are commercially available from different sources, such as such as Perkin-Elmer, Agilent, or Axon Instruments, etc., and examples of typical scanners are described in U.S. Pat. Nos. 5,091,652; 5,760,951, 6,320,196 and U.S. Pat. No. 6,355,934.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent. The term "evaluating a pixel" and grammatical equivalents thereof, are used to refer to measuring the strength, e.g., magnitude, of pixel signal to determine the brightness of a corresponding area present on the surface of an object scanned.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station. In certain embodiments, a processor may be a "signal processor", where a signal processor receives input signals and processes those signals. A signal processor may programmed or hard wired to perform one or more mathematical functions, such as those described below. In certain embodiments, a signal processor may "integrate" a set of digital signals (e.g., a set of digital signals representing an analog signal or a digitized version of an analog signal). By "integrating" is meant that a set of digital signals is input into a signal processor and the signal processor provides an output signal, in certain embodiments a single output signal, that represents the set of input signals. In many embodiments, the input set of digital signals may be integrated by summing the set of input signals, however, other means for integrating (e.g., averaging, etc.) are well known in the art. If an analog signal is referred to as being integrated, then it is understood that the analog signal is first digitized (i.e., sampled) prior to integration. For example, if an analog signal for a pixel is to be integrated, the signal is first sampled and digitized to provide a set of digital signals, and those digital signals are integrated by a signal processor to provide an output signal, typically a binary signal, that represents a numerical evaluation of the overall magnitude of the input set of digital signals (thereby providing a numerical evaluation of the magnitude of the analog signal for the pixel). The output of a signal processor may be referred herein as "data", and may be stored in memory.

Data from reading an array may be raw data (such as fluorescence intensity readings for each feature in one or more color channels, or, for example, the output of a signal processor that has integrated a set of digital signals for a pixel) or may be processed data such as obtained by rejecting a reading for a feature which is below a predetermined threshold and/or forming conclusions based on the pattern read from the array (such as whether or not a particular target sequence may have been present in the sample). The data obtained from an array reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc. Data may represent a floating point number or integer, for example.

A set of digital signals for a pixel (or an analog signal represented thereby) may be "saturated", "partially-saturated" or "non-saturated" depending on the number of saturated digital signals within the set. The digital signals in a saturated set of digital signals are all saturated, none of the digital signals in a non-saturated set of digital signals are saturated, and some but not all of the digital signals within a partially-saturated set of digital signals are saturated. Saturated digital signals may be identified by virtue of the fact that they are at maximal magnitude, and non-saturated digital signals may be identified by virtue of the fact that they are below maximal magnitude.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "providing" encompasses such terms as "generating", "identifying" and "producing".

DETAILED DESCRIPTION OF THE INVENTION

Methods for evaluating a pixel signal produced during scanning of a chemical array are provided. In general, the methods involve producing at least two analog signals for a pixel using a multi-gain signal detection system, integrating at least one of these signals, and outputting a single integrated signal representing the pixel. In many embodiments, the methods involve detecting, integrating and outputting a signal for a non-saturated input signal for the pixel. Also provided are systems and programming products for performing the subject methods, and an array scanner containing these systems and programming products. The subject invention finds use in a variety of different applications, including both genomics and proteomics applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, system and methods aspects of the invention are first described. This discussion is followed by a description of suitable hardware for use in the invention.

The following U.S. patent applications are herein incorporated by reference in their entireties for all purposes: 10/912,6561, entitled: "Methods and Compositions for Assessing Partially Saturated Pixel Signals", filed Aug. 4, 2004; 10/912,463, entitled: "Detection of Feature Boundaries Pixels During Array Scanning", filed Aug. 4, 2004; and 10/912,027, entitled: "Filtering of Pixel Signals During Array Scanning", filed Aug. 4, 2004. The following published U.S. patent applications are incorporated by reference in their entirety, including all definitions, for all purposes: Ser. No. 10/086,932 (filed on Feb. 28, 2002 and published as 20030165871), Ser. No. 10/261,563 (filed on Sep. 30, 2002 and published as 20040064264), Ser. No. 10/212,191 (filed on Jul. 31, 2002 and published as 20040023224), Ser. No. 10/210,848 (filed on Jul. 31, 2002 and published as 20040021911), Ser. No. 10/137,658 (filed on Apr. 30, 2002 and published as 20030203371) and Ser. No. 10/086,658 (filed on Feb. 28, 2002 and published as 20030168579).

Methodology

As discussed above, the invention provides methods for evaluating (e.g., producing a numerical evaluation of the brightness of) a pixel during scanning of a chemical array. In one embodiment, and with reference to FIG. 1, the method involves: a) producing a plurality of analog signals, e.g., signals 12 and 16, for a pixel using a multi-gain signal detection system 8, b) digitizing these analog signals using a converter (such as, for example, by using a corresponding plurality of analog-to-digital converters, e.g., 18 and 20), and, c) integrating and outputting a single integrated signal for one of the digitized signals 24 using a digital signal processor (DSP) 22. In certain embodiment, the DSP 22 determines whether a signal is a non-saturated signal (e.g., signal 12) or a saturated signal (e.g., signal 16) or a partially saturated signal (not shown), and, if any non-saturated signals are detected, a single non-saturated signal is integrated and output. Accordingly, the methods find particular use in evaluating an at least partially saturated pixel, where an "at least partially saturated pixel" is a pixel represented by one or more signals that is at least partly saturated (including fully saturated), i.e., at least at a maximum amplitude.

In the subject invention, light emitted from the surface of a chemical array enters a "multi-gain photodetection system", where such a system contains at least one multi-gain system component that inputs a single signal, e.g., a light signal (in the case of a light detector, for example), a current signal (in the case of a current-to-voltage converter, for example), or a voltage signal (in the case of a voltage amplifier, for example), and outputs a plurality of analog signals (i.e., 2 or more, e.g., 3, 4, 5, 6, 7, 8, 9, 10, about 12 about 16, about 20 or more, sometimes up to about 50 or more analog signals) that are different from each other only in terms of their magnitude. Such a system usually contains a single multi-gain system component that inputs a single analog signal (e.g., a light, current, or voltage signal) and outputs multiple analog signals that are proportional to the input signal, but at different magnitudes (except where an output signal may be saturated). Exemplary gain settings may differ by a factor of about 2 or more, of about 5 or more, about 10 or more, about 50 or more, about 100 or more, about 500 or more, about 1000 or more, about 5000 or more, about $1\times10^4$ or more, about $5\times10^5$ or more, $1\times10^6$ or more, $5\times10^7$ or more, usually up to about $1\times10^8$ or more. In other words, output signals of a multi-gain system component usually differ from each other in magnitude by at least about 2-fold, by at least about 5-fold, by at least about 10-fold, by at least about 50-fold, etc. In certain embodiments, a multi-gain photodetection system may contain two or more single-gain system components set at different gains. For example, a subject system may contain two or more detectors, two or more current-to-voltage converters or two or more voltage or current amplifiers at different gain settings, etc., each set at a different gain. As mentioned above, the signal input for most embodiments of the subject multi-gain photodetection systems is a single wavelength of light, corresponding to a single "channel" of light, as is commonly referred to in chemical array scanner arts. For example, "red" and "green" light emitted from fluorescent cyanine dyes, for example, may separately serve as an input light for the subject system.

Figure 2:
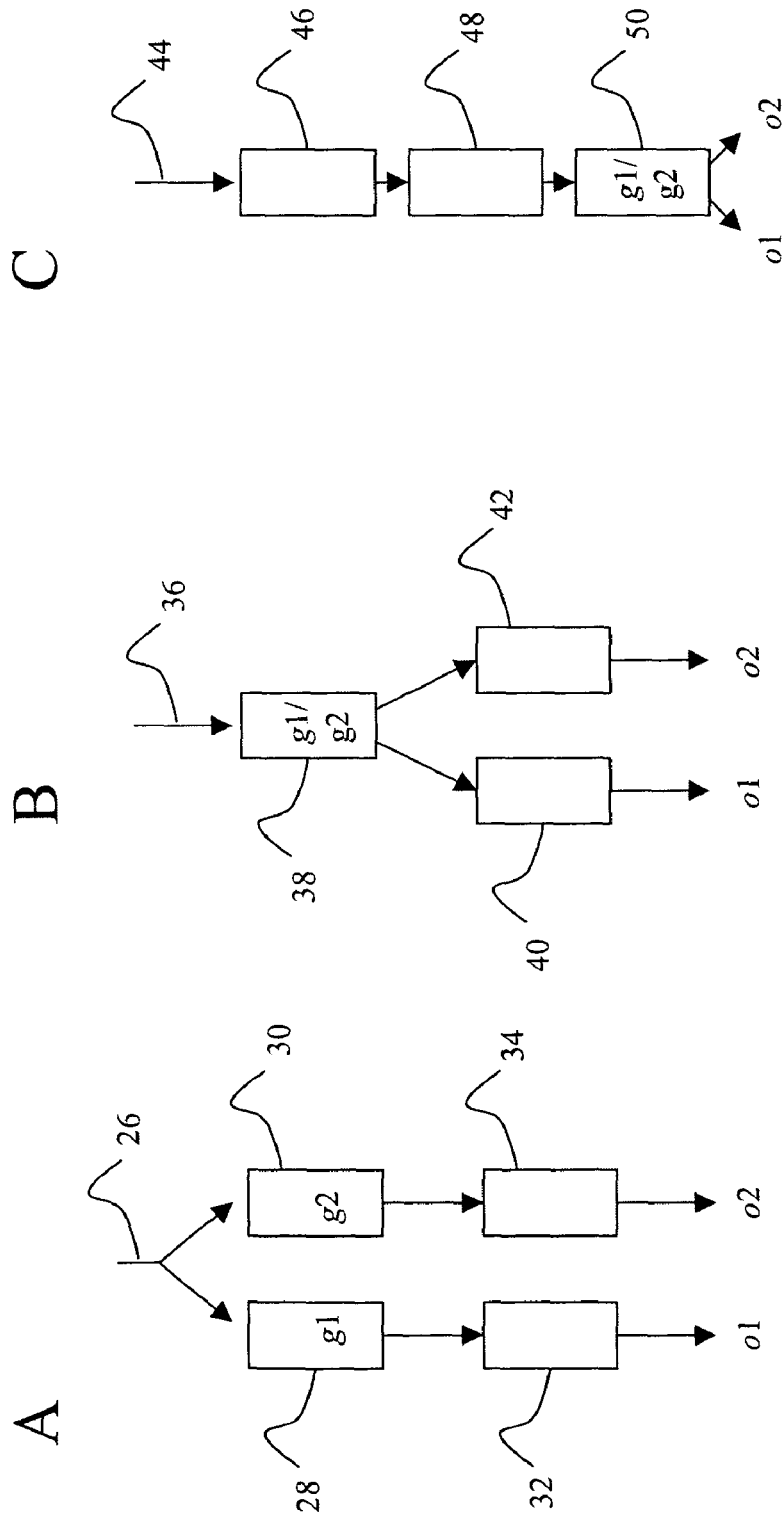
FIG. 2 is three panels of figures, A, B and C, and schematically illustrates several embodiments of the multi-gain detection systems described herein.

Exemplary, non-limiting, multi-gain photodetection systems useful in the subject methods are shown in FIG. 2. In panel A of FIG. 2, light signal 26 enters two or more detectors 28 and 30 set at different gains, e.g., g1 and g2. In this embodiment, the outputs of detectors 28 and 30 are analog current signals, and these outputs are input into current-to-voltage converters 32 and 34 to provide two analog voltage signal outputs o1 and o2 that differ in magnitude according to g1 and g2. In panel B of FIG. 2, light signal 36 enters a multi-gain light detector 38 set at a plurality of different gains, e.g., g1 and g2. In this embodiment, the outputs of detector 38 are two analog current signals, and these outputs are input into current-to-voltage converters 40 and 42 to provide two analog voltage signal outputs o1 and o2 that differ in magnitude according to g1 and g2. In panel C of FIG. 2, light signal 44 enters single gain detector 46, and the output of this detector, an analog current, is input into a current-to-voltage converter 48 to provide an analog voltage. This analog voltage is input into a multi-gain amplifier 50 set at a plurality of different gains, e.g., g1 and g2, and the amplifier outputs signals o1 and o2 that differ in magnitude according to g1 and g2. The output signal of the subject system may be any electrical signal (e.g., voltage, current, etc.). However, in many embodiments, the output signals of the system are voltage signals.

Returning to FIG. 1, the general methodology employed in the subject invention is described in more detail.

The graphs shown in FIG. 1 plot signal magnitude (i) versus time (t) for a pixel, which, in this figure, is represented by a period of time that a light signal is detected. In general, saturated pixels correspond to bright areas of a scan of the surface of an array, and an illustration of a light signal that may give rise to a saturated pixel is shown as element 6 of graph 2 in FIG. 1. This graph shows an exemplary light signal 6, relative to the maximum intensity of light detectable by typical prior art detector systems 4. Some of the light signal is beyond the detection limit of the typical detector system.

Light signal 6 is processed by multi-gain photodetection system 8, having multiple analog output signals, e.g., outputs o1 and o2. In this example, output o1 is at a lower magnitude than output o2, and represents non-saturated signal 12, as shown in graph 10. Part of the analog signal output o2 is maximal and "flat", indicating that the signal is saturated. Accordingly, output o2, as indicated in graph 14, is saturated. The outputs of system 8 (e.g., o1 and o2) are independently sampled and digitized by analog-to-digital converters (A/D converters), e.g., elements 18 and 20. The outputs of the A/D converters are then input into the same digital signal processor 22, processed and a single output from the DSP 22 is produced. The output is generally in the form of a numerical evaluation of a pixel 24. In one embodiment, a single output from the multi-gain detection system is integrated and output by the DSP 22 in the form of data. For example, each pixel may be associated with a numerical evaluation, e.g., an integer or floating point number, representing the integrated scan signal from a region on the surface of an object being scanned (for example a chemical array). This numerical evaluation may be stored in a memory.

In certain embodiments it is desirable to normalize the output of a subject processor so that the output is directly comparable to other outputs obtained using a different gain. Normalizing the outputs may be achieving by, for example, normalizing by the channel gain or multiplying the numerical evaluation obtained from lower gain channel by the ratio of the highest gain channel to the lower channel's gain. However, in other embodiments, the gain setting that was used to obtain the numerical evaluation is indicated, i.e., tagged, with the numerical evaluation in the processor output, and the normalization may happen at another time (e.g., by data extraction or data analysis software). The gain used to produce a numerical evaluation may be indicated using unused bits of a binary code representing the numerical evaluation.

In one embodiment, the digital signal processor 22 is programmed to integrate and output a signal corresponding to a non-saturated input signal. Accordingly, in many embodiments, the processor 22 is programmed to detect an input digital signal that is non-saturated, and select that non-saturated input signal for integration and output. In one embodiment, if a plurality (i.e., more than one) of non-saturated input signals are input into the detector, the DSP 22 integrates the non-saturated signal having the highest magnitude. In other words, if a single non-saturated input signal for a pixel is detected, it is integrated by DSP 22 to provide a numerical evaluation of the pixel. If a plurality of sets of unsaturated input signals for a pixel are detected, in certain embodiments, the set of unsaturated input signals that has the greatest overall magnitude is integrated to provide a numerical evaluation of the pixel. In certain embodiments, the non-saturated input signals are distinguished from the saturated signals by virtue of the fact that non-saturated signals are not saturated. In other words, in certain embodiment, non-saturated signals may be detected because they are not at maximal magnitude. Accordingly, in certain embodiments, for each plurality of signals input into the processor, the non-saturated signals can be identified by detecting the saturated signals.

The methods find use in integrating signals for pixels that are fully or partially saturated (i.e., the signal for a pixel is more than about 5%, more than about 10%, more than about 10%, more than about 20%, more than about 40%, more than about 60%, more than about 80%, more than about 90%, more than about 95%, up to 99% or 100% saturated) under scanning conditions that are typically used during array scanning, e.g., Cheung et al., Nature Genetics 1999, 21: 15-19.

In certain embodiments, the subject methods may be done in "real-time". In other words, the single integrated signal or data for a pixel obtained using the subject methods is generally output from the processor prior to processing of the signals for the next pixel. In particular embodiments for example, data obtained from a signal may be stored in a buffer and analyzed while accumulating data from a future pixel, e.g., the next pixel scanned.

Accordingly, in view of the foregoing, the invention provides methods of evaluating a pixel (e.g., identifying and integrating a non-saturated signal for a pixel), and a system for performing the methods. As illustrated in FIG. 2, the system contains at least: a) multi-gain detection system (such as a multi-gain photodetection system) 8, b) one or more converters, e.g., a plurality of converters, for converting an analog signal to a digital signal (e.g., such as A/D converters 18 and 20), and c) a digital signal processor 22 that is programmed to integrate a signal and output data corresponding to a non-saturated input signal. Depending on how the system is configured, other system components may be present in the system, such as a current-to-voltage, voltage-to-current integrator, signal amplifiers, other processors, and the like.

Computer-related Embodiments

The invention also provides a variety of computer-related embodiments. Specifically, the methods described may be executed by a digital system processor in accordance with instructions from a computer program product. Accordingly, the invention provides a digital signal processor programmed to input multiple digital signals for a pixel, process these signals to identify a non-saturated input signal, and output data corresponding to that single non-saturated input signal, as discussed above. The computer program product comprises programming coded onto computer-readable medium, and the programming and the digital system processor may be part of a computer-based system.

In certain embodiments, the above methods are coded onto a computer-readable medium in the form of "programming" or "programming products" as instructions, where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming, or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

Optical Scanners

The subject systems and methods find particular use in chemical array scanners. Accordingly, also provided by the subject invention is an array scanner that contains a system for performing the subject methods described above. Typically, such scanners have a laser excitation system for emitting light from the surface of an array, hardware for performing the methods described above, and, usually, a storage medium for storing data produced by scanning. A scanner may also contain or communicate with a processor including programming for executing the subject methods. Since array scanners typically measure at least two, and sometimes three, four or five or more wavelengths of light from the surface of an array, a subject scanner may have a corresponding number (e.g., 2, 3, 4, 5, or more) systems for performing the subject methods. In many embodiments, a subject scanner will contain typically contain at least two such systems, corresponding to the "red" and "green" channels of light emitted in typical array experiments (Cheung et al., Nature Genetics 1999, 21: 15-19).

Any optical scanner or device may be provided to include the above programming. Representative optical scanners of interest include those described in U.S. Pat. Nos. 5,585,639; 5,760,951; 5,763,870; 6,084, 991; 6,222,664; 6,284,465; 6,329,196; 6,371,370 and 6,406,849—the disclosures of which are herein incorporated by reference. An exemplary optical scanner as may be used in the present invention is shown in FIG. 3.

Figure 3:
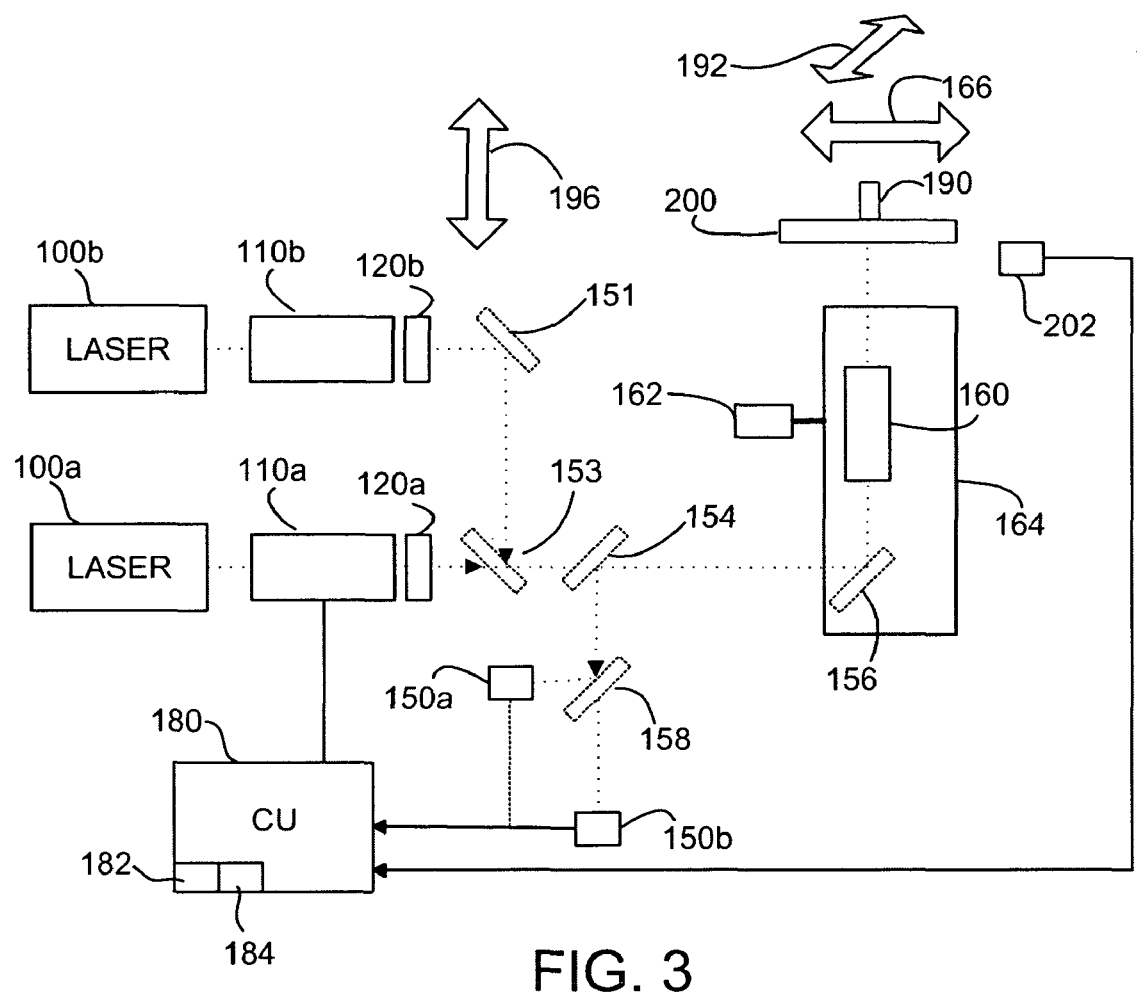
FIG. 3 schematically illustrates an apparatus as may be used in the present invention.

Referring now to FIG. 3, an exemplary apparatus of the present invention (which may be generally referenced as an "array scanner") is illustrated. A light system provides light from a laser 100 which passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light spot exiting from the attenuator. The remainder of the light from both lasers 100a, 100b is transmitted through a dichroic beam splitter 154, reflected off fully reflecting mirror 156 and focused onto an array mounted on holder 200, using optical components in beam focuser 160. Light emitted (in particular, fluorescence) at two different wavelengths (e.g., green and red light) from features on the array, in response to the interrogating light, is imaged using the same optics in focuser/scanner 160, and is reflected off mirrors 156 and 154. The two different wavelengths are separated by a further dichroic mirror 158 and are passed to respective detectors 150a and 150b. Depending on how the subject methods are implemented, a subject scanner may contain more than one of 150a, and more than one of 150b, or, in alternate embodiments, 150a and 150b may be multi-gain detectors.

More optical components (not shown) may be used between the dichroic and each detector 150a, 150b (such as lenses, pinholes, filters, fibers, etc.) and each detector 150a, 150b may be of various different types (e.g., a photo-multiplier tube (PMT), or photodiode or avalanche photodiode device (APD), such as a charge-coupled device (CCD), a charge-injection device (CID), or a complementary-metal-oxide-semiconductor detector (CMOS) device), CCD or an avalanche photodiode (APD). All of the optical components through which light emitted from an array 12 or calibration member 230 in response to the illuminating laser light, passes to detectors 150a, 150b, together with those detectors, form a detection system. This detection system has a fixed focal plane. A scan system causes the illuminating region in the form of a light spot from each laser 100a, 100b, and a detecting region of each detector 150a, 150b (which detecting region will form a pixel in the detected image), to be scanned across multiple regions of an array or array package mounted on holder 200. The scanned regions for an array will include at least the multiple features of the array. In particular the scanning system is typically a line by line scanner, scanning the interrogating light in a line across an array when at the reading position, in a direction of arrow 166, then moving ("transitioning") the interrogating light in a direction into/out of the paper as viewed in FIG. 3 to a position at an end of a next line, and repeating the line scanning and transitioning until the entire array has been scanned.

This scanning feature is accomplished by providing a housing 164 containing mirror 158 and focuser 160, which housing 164 can be moved along a line of pixels (i.e., from left to right or the reverse as viewed in FIG. 3) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The scanner of FIG. 3 may further include a reader (not shown) which reads an identifier from an array package. When identifier 40 is in the form of a bar code, that reader may be a suitable bar code reader.

Of course, the movements 166 and 192 may be accomplished by actuating holder 200 or housing 164 alone. Still further, the movement roles described for each element above may be swapped.

The system may also include detector 202, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, autofocus system 202 may contain a position detector e.g. a quadrature position encoder, also feeding back to the CU measures the absolute position (i.e., relative to the apparatus) of the servo-controlled adjuster 190. As above with respect to movements 166 and 192, it should be observed that focus servo control movement 196 may occur in connection with housing 164 instead of the holder, or, if the detection system is not a fixed focal plane system, by an adjustment of laser focuser 160. Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors.

Controller 180 of the apparatus is connected to receive signals from detectors 150a, 150b (these different signals being different "channels"), namely a signal which results at each of the multiple detected wavelengths from emitted light for each scanned region of array 12 when at the reading position mounted in holder 200. Controller 180 also receives the signal from autofocus detector 202, and provides the control signal to EOM 110, and controls the scan system. Controller 180 contains all the necessary software to detect signals from detector 202, and regulate a motorized or servo-controlled adjuster 190 through a control loop. Controller 180 may also analyze, store, and/or output data relating to emitted signals received from detectors 150a, 150b in a known manner.

Controller 180 also includes a programmable digital signal processor for performing the methods described above, and usually includes plurality of analog-to-digital converters, and other components of a multi-gain detection system (such as a multi-gain photodetection system), e.g., a current-to-voltage converter, voltage amplifier, etc., as desired, a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40).

In one mode of operation, an array in a package is typically first exposed to a liquid sample. This liquid sample may be placed directly on the array or introduced into a chamber through a septa in the housing of the array. After a time to allow, for example, hybridization, the array may then be washed and scanned with a liquid (such as a buffer solution) present in the chamber and in contact with the array, or it may be dried following washing. After mounting a given array in cradle 200 (either with the array features on the glass surface nearer to, or further from, the lens—depending, at least, upon the lens setup) the identifier reader may automatically (or upon operator command) read an identifier from the array package, which may be used to e.g. retrieve information on the array layout from a database containing the identifier in association with such information. Such a database may be a local database accessible by controller 180 (such as may be contained in a portable storage medium in drive 182.

The saved results from a sample exposed array, read with the methods described above, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

While it is noted that a scanner that reverses scanning direction at the end of each scan line (i.e. a bi-directional scanner) is disclosed, unidirectional scanners also find use with the methods of the invention.

Utility

The subject array scanners find use in a variety applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays;

nucleic acid sequencing assays, and the like. References describing methods of using arrays in various applications include U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. Certain embodiments of the invention may involve transmitting data obtained from a method described above from a first location to a remote location. Certain other embodiments of the invention may involve receiving, from a remote location, data obtained from a method described above.

In reading the array, pixel signals are usually processed using the methods described above.

It is further noted that aspects of the invention may be applicable to a variety of optical scanners including those that detect chemiluminescent or electroluminescent labels. The present invention will be applicable to such scanners where powering down the scanner will result in lifetime savings, as exemplified above.

Kits

Kits for use in connection with the subject invention may also be provided. Such kits usually include at least a computer program product comprising computer readable medium including programming as discussed above and, in certain kits, instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g., via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the invention. As with the instructions, the means for obtaining the instructions and/or programming is generally recorded on a suitable recording medium.

In addition to the subject programming and instructions, the kits may also include one or more reference arrays, e.g., two or more reference arrays for use in testing an optical scanner after software installation.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A system comprising:
    a) a multi-gain detection system that produces a plurality of analog signals representative of a pixel, wherein said multi-gain detection system inputs a single signal and outputs a plurality of analog signals representative of said pixel;
    b) a converter for digitizing the plurality of analog signals to produce a set of digital signals for each analog signal;
    c) a signal processor that:
        i) identifies a set of non-saturated digital signals for said pixel,
        ii) integrates said set of non-saturated digital signals for said pixel to evaluate said pixel; and
        iii) outputs data for said pixel; and
    a data storage means configured to store said data on a computer-readable medium comprising a permanent memory.

2. The system of claim 1, wherein said converter comprises a plurality of analog-to-digital converters.

3. The system of claim 1, wherein said multi-gain detection system comprises a photodetector.

4. The system of claim 1, wherein said multi-gain signal detection system comprises a single multi-gain detector.

5. The system of claim 1, wherein said multi-gain detection comprises a plurality of detectors, each having a different gain setting.

6. The system of claim 1, wherein said multi-gain signal detection comprises a plurality of current-to-voltage converters.

7. The system of claim 1, wherein said multi-gain signal detection comprises a multi-gain voltage amplifier.

8. A chemical array scanner comprising:
    a laser excitation system;
    the system according to claim 1.

9. The chemical array scanner of claim 8, wherein said system produces data for said array, and said scanner comprises a storage medium for storing said data.

10. The chemical array scanner of claim 9, wherein said storage medium is computer memory.

11. A method comprising:
    producing a plurality of analog signals for a pixel using a multi-gain signal detection system, wherein said multi-gain detection system inputs a single signal and outputs a plurality of analog signals representative of said pixel;
    identifying a non-saturated analog signal for said pixel;
    integrating said non-saturated analog signal to produce data; outputting said data; and
    storing said data on a computer-readable medium comprising a permanent memory.

12. The method of claim 11, wherein said plurality of signals are a plurality of voltage or current signals.

13. The method of claim 11, wherein said method comprises:
    providing for detection of a set of non-saturated digital signals for said pixel;
    integrating a set of digital signal that is non-saturated; and
    outputting a single integrated signal for said set of digital signals that are not saturated.

14. The method of claim 11, wherein said single integrated signal is data, and said method further comprises storing said data on a computer-readable medium.

15. A computer-readable medium comprising:

programming for execution by a signal processor to produce data for a pixel represented by multiple sets of digital signals of varying magnitude, said programming comprising:

instructions for integrating a set of non-saturated digital signals for said pixel to produce an integrated signal representing said signal; and instructions for outputting said integrated signal to produce data for said pixel.

16. The computer-readable medium of claim 15, wherein said computer-readable medium further comprises instructions for executing said programming when a non-saturated signal for said pixel is detected.

17. The computer-readable medium of claim 15, wherein said output is tagged to indicate that said data is from a saturated pixel.

18. A processor comprising the computer-readable medium of claim 15.

19. A chemical array scanner comprising the processor of claim 18.

20. A kit for use in a chemical array optical scanner, said kit comprising:

(a) the computer-readable medium according to claim 15; and (b) at least one chemical array.

21. The method of claim 11, further comprising scanning a chemical array.

* * * * *